United States Patent
Case et al.

(10) Patent No.: US 7,153,324 B2
(45) Date of Patent: Dec. 26, 2006

(54) PROSTHETIC VALVE DEVICES AND METHODS OF MAKING SUCH DEVICES

(75) Inventors: Brian C. Case, Bloomington, IN (US); Jacob A. Flagle, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 103 days.

(21) Appl. No.: 10/909,153

(22) Filed: Jul. 30, 2004

(65) Prior Publication Data
US 2005/0027348 A1    Feb. 3, 2005

Related U.S. Application Data

(60) Provisional application No. 60/491,595, filed on Jul. 31, 2003.

(51) Int. Cl.
*A61F 2/06* (2006.01)

(52) U.S. Cl. .................... 623/1.24; 623/1.11

(58) Field of Classification Search ...... 623/1.21–1.24, 623/2.1, 2.14–2.18
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,275,826 A | 1/1994 | Badylak et al. |
| 5,352,463 A | 10/1994 | Badylak et al. |
| 5,411,552 A | 5/1995 | Andersen et al. |
| 5,516,533 A | 5/1996 | Badylak et al. |
| 5,840,081 A | 11/1998 | Andersen et al. |
| 5,855,601 A | 1/1999 | Bessler et al. |
| 5,957,949 A | 9/1999 | Leonhardt et al. |
| 5,993,844 A | 11/1999 | Abraham et al. |
| 6,027,525 A | 2/2000 | Suh et al. |
| 6,126,686 A * | 10/2000 | Badylak et al. ............ 623/1.24 |
| 6,168,614 B1 | 1/2001 | Andersen et al. |
| 6,254,564 B1 | 7/2001 | Wilk et al. |
| 6,302,917 B1 | 10/2001 | Dua et al. |
| 6,375,989 B1 | 4/2002 | Badylak et al. |
| 6,440,164 B1 * | 8/2002 | DiMatteo et al. .......... 623/1.24 |

(Continued)

FOREIGN PATENT DOCUMENTS

WO    WO 88/00459    1/1988

(Continued)

OTHER PUBLICATIONS

Search Report and Written Opinion dated Dec. 12, 2004, for corresponding international application No. PCT/US2004/024730.

(Continued)

*Primary Examiner*—Thomas Barrett
(74) *Attorney, Agent, or Firm*—Brinks Hofer Gilson & Lione (57) ABSTRACT

Prosthetic valve devices for implantation in body vessels, and methods of making same, are provided. The device has a main body with first and second ends and defining a lumen, with the second end being inverted into the lumen. A valve is disposed at the second end. In multiple valve devices, valves are disposed at the first and second ends, and individually may be inverted into the lumen. The prosthetic valve devices may further include a support structure such as a stent. Methods of making a prosthetic valve device include providing a main body having first and second ends and defining a lumen, forming a valve at the second end, and inverting the second end into the lumen. Methods may further comprise forming multiple valves and may also include attaching a support structure.

10 Claims, 10 Drawing Sheets

U.S. PATENT DOCUMENTS

| | | |
|---|---|---|
| 6,494,090 B1 | 12/2002 | Lösing et al. |
| 6,572,650 B1 | 6/2003 | Abraham et al. |
| 6,582,462 B1 | 6/2003 | Andersen et al. |
| 6,582,642 B1 * | 6/2003 | Buzzell et al. .............. 264/167 |
| 6,653,291 B1 | 11/2003 | Badylak et al. |
| 2001/0010017 A1 | 7/2001 | Letac et al. |
| 2002/0032487 A1 | 3/2002 | Dua et al. |
| 2002/0177894 A1 | 11/2002 | Acosta et al. |
| 2003/0023303 A1 | 1/2003 | Palmaz et al. |
| 2003/0036795 A1 | 2/2003 | Andersen et al. |
| 2003/0060875 A1 | 3/2003 | Wittens |

FOREIGN PATENT DOCUMENTS

| | | |
|---|---|---|
| WO | WO 01/66190 A2 | 9/2001 |
| WO | WO 03/092554 A1 | 11/2003 |

OTHER PUBLICATIONS

Notification of Transmittal of the International Preliminary Report on Patentability dated Nov. 25, 2005 for International Application No. PCT/US2004/024730.

* cited by examiner

PROSTHETIC VALVE DEVICES AND METHODS OF MAKING SUCH DEVICES

RELATED APPLICATIONS

The present patent document claims the benefit of the filing date under 35 U.S.C. §119(e) of Provisional U.S. Patent Application Ser. No. 60/491,595, filed Jul. 31, 2003, which is hereby incorporated by reference in its entirety.

FIELD OF THE INVENTION

The present invention relates to medical devices, and in particular to prosthetic valve devices and methods of making such devices.

BACKGROUND OF THE INVENTION

By use of a closed circulatory system, animal bodies use many internal organs and vessels to transport fluids from one bodily location to another. Components of the circulatory system include the heart, blood vessels, and blood. The heart has valves (semilunar valves and atrioventricular valves) that regulate the flow of blood in the atria and the ventricles. Three examples of blood vessels are arteries, veins, and capillaries. Whereas arteries transport blood to organs throughout the body (i.e., away from the heart), veins carry blood back to the heart. Structurally, capillaries have an inner endothelium surrounded by a membrane, while arterial and venal walls have three layers: connective tissue forms the outer layer, while smooth muscle having elastic fibers forms the middle layer, and there is an innermost endothelium layer. Mammalian veins, such as human veins for example, have naturally occurring valves positioned along the length of the vessel.

Mammalian valves, such as human venous valves for example, act as one-way check valves that open to permit the flow of fluid in a first direction (e.g., muscles contract, squeeze the veins, and the valves—flaps of tissue—keep blood moving toward the heart), and quickly close upon a change in pressure, such as a transition from systole to diastole or when muscles relax or stop contraction, to prevent fluid flow in a reverse direction, i.e., retrograde flow.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of valve leaflets to close. Furthermore, the leaflets may become damaged, such as by formation of thrombus and scar tissue, which may also affect the ability of the valve leaflets to close. Once valves are damaged, venous valve insufficiency may be present and can lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed or replaced with autologous sections of veins with competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, the use of stents has been extended to treat aneurysms and to provide occlusion devices, among other uses.

Therefore, it is desirable to have prosthetic valve devices for implantation in a body vessel as taught herein, and methods of making such devices.

SUMMARY OF THE INVENTION

A prosthetic valve device for implantation in a body vessel is provided. In one embodiment, the device comprises a main body with first and second ends and defines a lumen. The second end is inverted into the lumen. A valve is disposed at the second end and is adapted to permit fluid flow through the lumen in a first direction and substantially prevent fluid flow through the lumen in a second, opposite direction.

In another embodiment, a prosthetic valve device according to the invention comprises a main body with first and second ends and defines a lumen. The second end is inverted into the lumen. A first valve is disposed at the first end and a second valve is disposed at the second end. The first and second valves are individually adapted to permit fluid flow through the lumen in a first direction and substantially prevent fluid flow through the lumen in a second, opposite direction.

In another embodiment, a prosthetic valve device according to the invention comprises a tubular main body with first and second ends. The main body defines a lumen. A valve is disposed at the second end and is adapted to permit fluid flow through a lumen in a first direction and substantially prevent fluid flow through the lumen in a second, opposite direction. The main body is attached to a support structure having proximal and distal ends. The proximal end of the support structure is disposed in the lumen of the main body, and the second end of the main body is inverted into the lumen of the main body, thereby enveloping the proximal end of the support structure.

Methods of making prosthetic valve devices are also provided. In one embodiment, a method according to the invention comprises providing a main body having first and second ends and defining a lumen and inverting the second end into the lumen to form a valve.

In another embodiment, a method according to the invention comprises providing a main body having first and second ends and defining a lumen. A valve is formed at the second end. The second end is inverted into the lumen.

In another embodiment, a method according to the invention comprises providing a main body sheet having first and second edges. Inverting the main body intermediate the first and second edges to form a tubular body having first and second ends and defining a lumen and a valve.

In another embodiment, a method according to the invention comprises providing a tubular main body having first and second ends and defining a lumen. A support structure having proximal and distal ends is provided. A valve is formed at the second end of the main body. The proximal end of the support structure is disposed in the lumen of the main body. The second end of the main body is inverted into the lumen and envelopes the proximal end of the support structure.

DETAILED DESCRIPTION OF EMBODIMENTS

The present invention relates to medical devices, and in particular to prosthetic valve devices and methods of making such devices. For the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, contain(s) and the variants thereof are intended to be open ended transitional phrases, terms, or words that do not preclude the possibility of additional steps or structure.

Figures 1, 2:
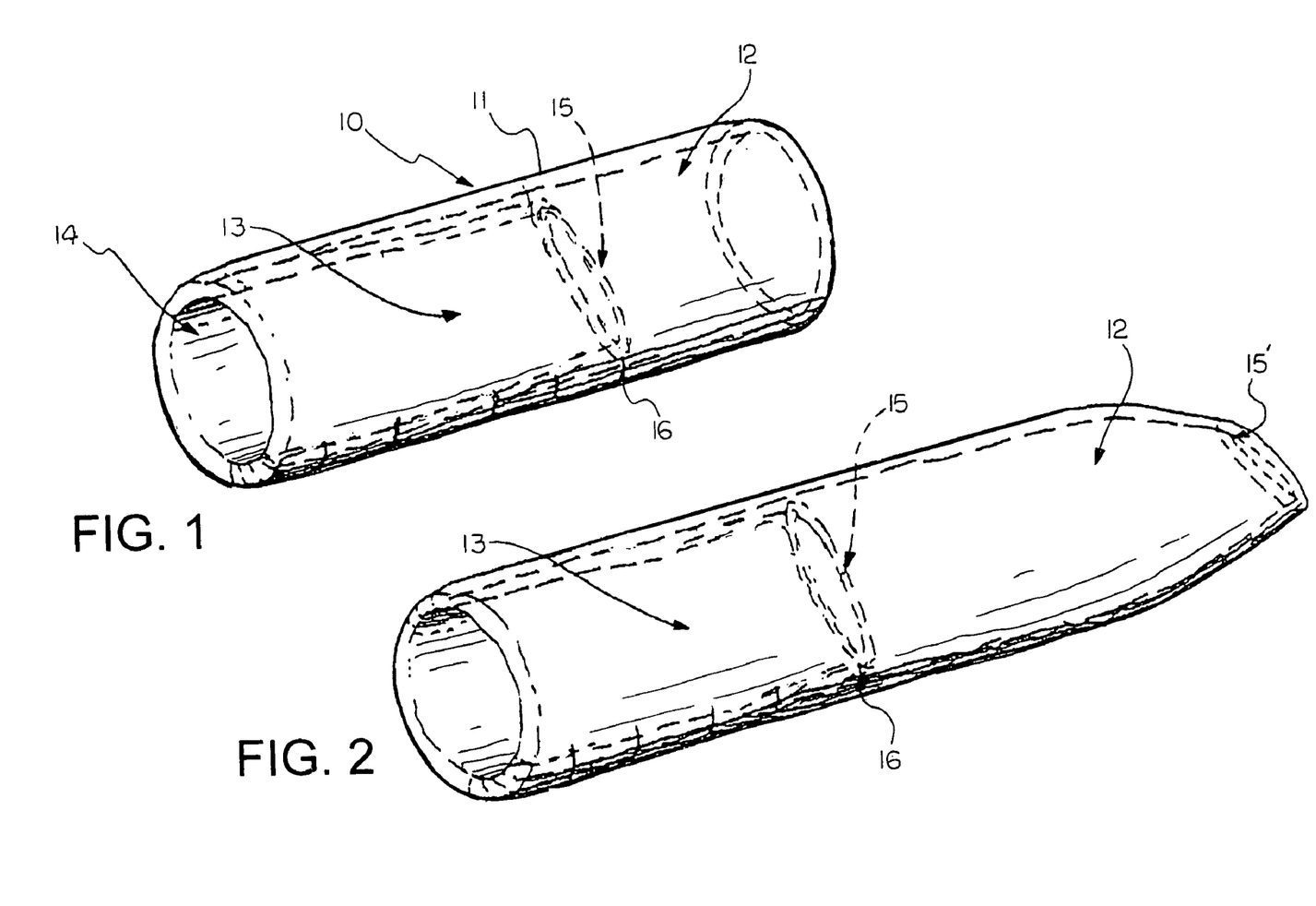
FIG. 1 is a perspective view of an embodiment of a prosthetic valve device according to one embodiment of the invention.
FIG. 2 is a perspective view of a prosthetic valve device according to another embodiment of the invention comprising two valves.

As illustrated in FIG. 1, a prosthetic valve device of an embodiment of the present invention comprises a main body 11 having first and second ends 12, 13 and defining a lumen 14, the second end 13 being inverted into the lumen 14. A valve 15 is disposed at the second end 13, and the valve 15 is adapted to permit fluid flow through the lumen in a first direction and substantially prevent fluid flow through the lumen in a second, opposite direction.

Optionally (not shown), the main body 11 has a sinus at or near the site of a valve. A sinus is a bulging or bowing (e.g., a nominal increase in the inner diameter) of the main body at or near the site of a valve. A sinus optionally is utilized in an embodiment of a prosthetic valve device with or without a support structure (as support structure is defined later).

Optionally, a prosthetic valve device includes one or more anchor points 16. The reference numeral for one anchor point 16 shown in FIGS. 1 and 2 is located at or near the valve 15, but it should be understood that anchor point(s) may be placed at the other hash marks depicted in FIGS. 1 and 2, as well as other figures herein. There may be more or fewer anchor points, and not limited to the positions where the hash marks are represented in these figures. Also, the anchor points can be anywhere from a valve orifice to a base of the pocket—in a valve configuration (e.g., a bicuspid configuration) for convenience of the reader the valve orifice and active leaflets move for passage of fluid downstream in the vessel and the base of the pocket is defined to be a portion of the valve positioned upstream of the valve orifice (i.e., axially speaking, if fluid flows distally, then the base of the pocket is proximal to the valve orifice). The anchor points help to control or prevent prolapse, which may include sliding and/or eversion of the valve, for example. Additionally, an anchor point if desired may optionally be configured to be capable of allowing some sliding and/or movement (e.g., some give and take) of adjacent surfaces and/or interfaces or the anchor point may be relatively taut. By way of example only, anchor point(s) may comprise any suitable means for anchoring, including but not limited to sutures, wires, crimping, band(s), adhesives, tissue welding, chemical cross-linking, heat source, light source, radiofrequency, lasering, or other energy source. As used herein, anchoring shall refer to and include joining, connecting, attaching, and holding by way of examples.

Main Body

The main body 11 has a single layer, but may have multiple layers or even a varying number of layers along its length. Depending on the body vessel into which the device is implanted, the main body may be relatively straight or have a bend, curve, or angle to it. The main body may be configured for a device to be implanted in body vessels of the circulatory system having a valve, as in the heart, blood vessels, vein, or capillary. The invention is not limited to vascular purposes, and should be understood as being of or relating to any vessel or organ for the conveyance, regulation, flow, or movement of bodily fluid of an animal.

The main body may be made of any suitable material, such as connective tissue, fibers, or any suitable material (natural, synthetic, or combination thereof) that is pliable, strong, resilient, elastic, and flexible. The material should be biocompatible, or should be able to be made biocompatible, such as by coating, chemical treatment, or the like. Thus, in general, the material may comprise a synthetic biocompatible material that may include, for example, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof, polylactic acid, polyglycolic acid or copolymers thereof, a polyanhydride, polycaprolactone, polyhydroxy-butyrate valerate, polyhydroxyalkanoate, or another polymer able to be made biocompatible.

In certain embodiments of the invention, the material is comprised of a naturally derived or synthetic collagenous material, for instance, an extracellular matrix material. Suitable extracellular matrix materials include, for instance, submucosa (including for example small intestine submucosa (SIS), stomach submucosa, urinary bladder submucosa, or uterine submucosa), renal capsule membrane, dura mater, pericardium, serosa, peritoneum or basement membrane materials, including liver basement membrane. Extracellular collagen matrices (ECM) such as SIS or other types of submucosal-derived tissue may have a remodelable quality that can be used as scaffolding to induce the growth and proliferation of neurological related tissues and to serve as a matrix for the regrowth of native tissues over time, which tissue may be referred to as tissue derived from ECM or SIS, or may be cross linked to affect the degree of remodelability. The material used herein may be made thicker by making multilaminate constructs. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. No. 6,206,931, which is hereby incorporated by reference in its entirety.

The main body may be formed by extrusion. Also, sheets of material may be stamped and then used to form the main body. For example, the main body may be formed by rolling a single sheet's edges toward each other and then joining them by any suitable means for joining, such as sewing, adhesives, wires, tissue welding, chemical cross-linking, heat source, light source, radiofrequency, lasering, or other energy source. As used herein, joining shall refer to and include connecting, attaching, anchoring, and holding by way of examples. Alternatively, the main body may be formed from two sheets, wherein edges (e.g., sides) from a first sheet are joined to edges from a second sheet by the aforesaid means for joining. Similarly, the main body may be formed from several sheets.

Figures 1A, 1B:
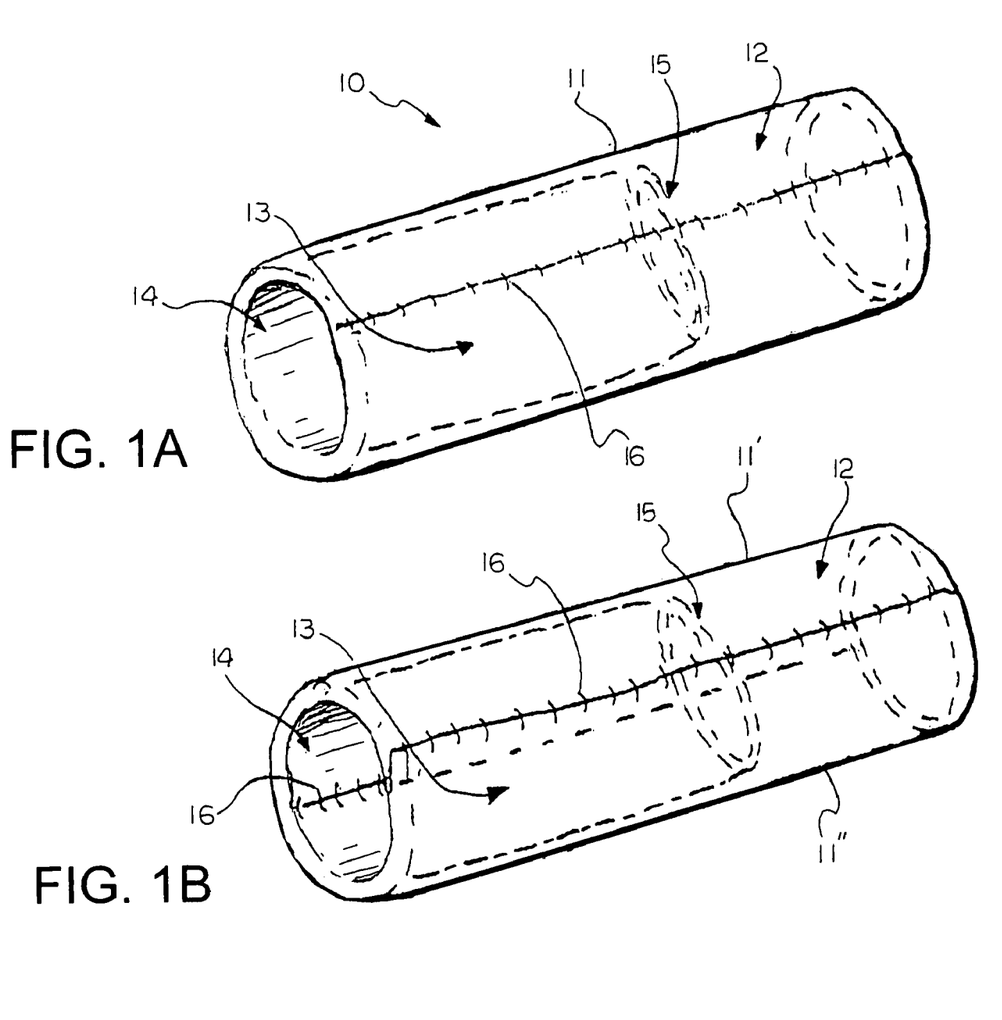
FIG. 1A is an alternative embodiment of a prosthetic valve device according to another embodiment of the invention formed from material comprising a sheet of main body.
FIG. 1B is an alternative embodiment of a prosthetic valve device according to another embodiment of the invention formed from material comprising two sheets of main body.

For example, the embodiments of prosthetic valve devices as shown in FIGS. 1 and 2 are made from a tube of main body 11. Optionally, the device may be made from a single substantially flat sheet of main body 11 joined together as shown in FIG. 1A. Another embodiment of the device is made from two substantially flat sheets of main body 11' and 11" joined together as depicted in FIG. 1B. In FIGS. 1A and 1B, the means for joining the sheet(s) of main body include but are not limited to sutures, wires, crimping, band(s), adhesives, tissue welding, chemical cross-linking, heat source, light source, radiofrequency, lasering, or other energy source. Also, those means for joining the sheets may also serve as anchor points 16. Embodiments comprising one or more sheets of main body material, such as FIGS. 3D and 3E, are discussed below and incorporated herein by reference.

Lumen

As shown in FIG. 1, the main body 11 may be generally tubular. As used herein, the term "tubular" includes any tube-like, cylindrical, round, oblong, or elongated structure that includes a lumen 14. Depending on the vessel into which the device is to be implanted, the main body may comprise other configurations having a lumen 14, as when the cross-sectional view is generally square, rectangular, ovulate, triangular, or crescent as specific but non-limiting examples of embodiments that include a lumen 14. The lumen 14 is understood to be any chamber, channel, opening, bore, orifice, flow passage, passageway, or cavity.

The inner diameter of the lumen need not be constant. For example, the main body 11 optionally has a sinus (not shown) at or near the site of a valve, whereby there is a bulging or bowing (e.g., a nominal increase in the inner diameter) of the main body and/or lumen at or near the site of a valve.

Valve

A valve 15 may comprise flap(s), fold(s), or leaflet(s). The valve can be formed from the main body 11 at one end by any suitable means for forming, including adhesives, tissue welding, wires, crimping, bands, chemical cross-linking, heat source, light source, radiofrequency, lasering or other energy source, sewing main body 11 material onto itself, molding and shaping it onto a mandrel, snipping it to define a valve, sewing it to a support member 40 (described below) that places the main body 11 material into a valve configuration. Additionally, where two sheets forming the main body are rectangular, corners may be cut away before joining the edges (e.g., sides) of the sheets.

Anchor points (as previously described) may be utilized to maintain valve stability by controlling prolapse. Also, the valve can be attached either to the main body or to the support member. Attachment may be carried out by any suitable means for attaching, such as sewing, adhesives, wires, crimping, bands, tissue welding, chemical cross-linking, heat source, light source, radiofrequency, lasering, or other energy source for attaching the valves to the main body. As used herein, attaching shall refer to and include joining, connecting, anchoring, and holding by way of examples. Optionally, the valve material may be made (or capable of being made) sufficiently pliable yet strong and rigid enough to control prolapse.

Figure 1C:
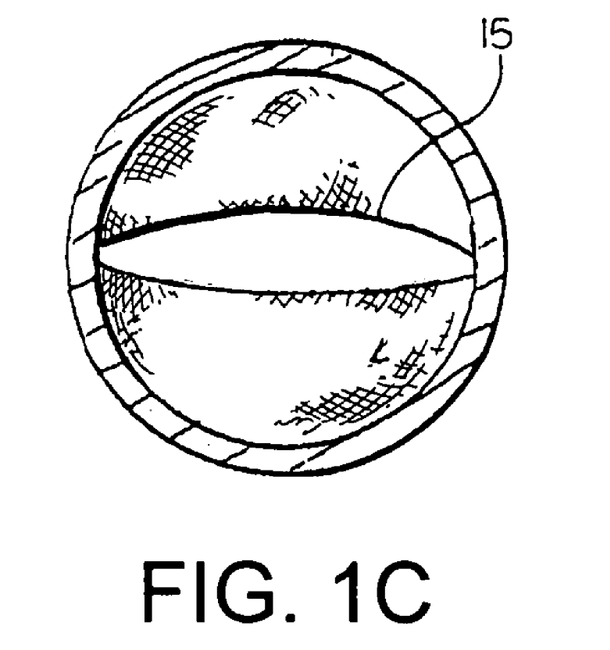
FIG. 1C is an alternative embodiment of a prosthetic valve device according to another embodiment of the invention comprising a taut valve.
Figure 1D:
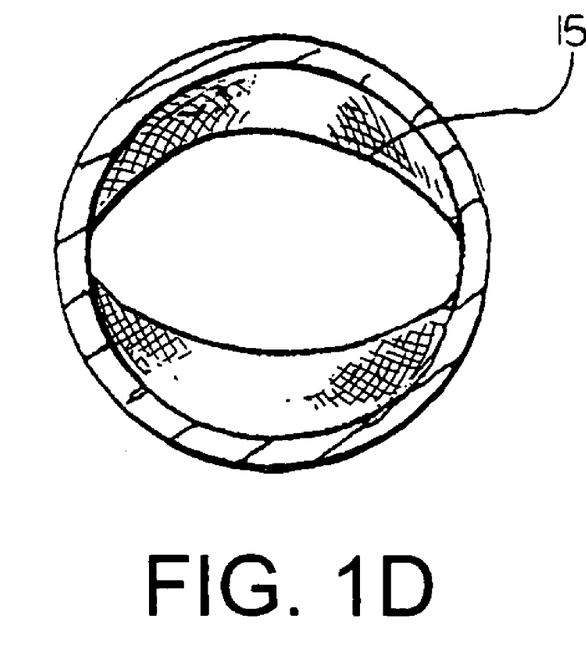
FIG. 1D is an alternative embodiment of a prosthetic valve device according to another embodiment of the invention comprising a loose valve.

FIGS. 1 and 2 show a main body having first and second ends 12, 13 and a valve 15 positioned at the second end 13, and FIG. 2 further shows disposing a valve 15' at the first end 12. The orifice of the valves may be changed (reduced or increased) depending on whether a taut or loose valve is desired. A taut or a loose valve may be utilized for one or more of the valves in the embodiment such as FIG. 2 (i.e., in a configuration with two valves, one of the valve orifices could be taut while the other may be loose or they could be the same). FIG. 1C is a cross-sectional view of an embodiment of FIG. 1 having a taut leaflet 15. FIG. 1D is a cross-sectional view of an embodiment of FIG. 1 having a loose leaflet 15. Therefore, wherever a valve is illustrated in the other figures, it should be understood that the valve may be taut or loose.

Fluid Flow

Figures 9, 10, 11:
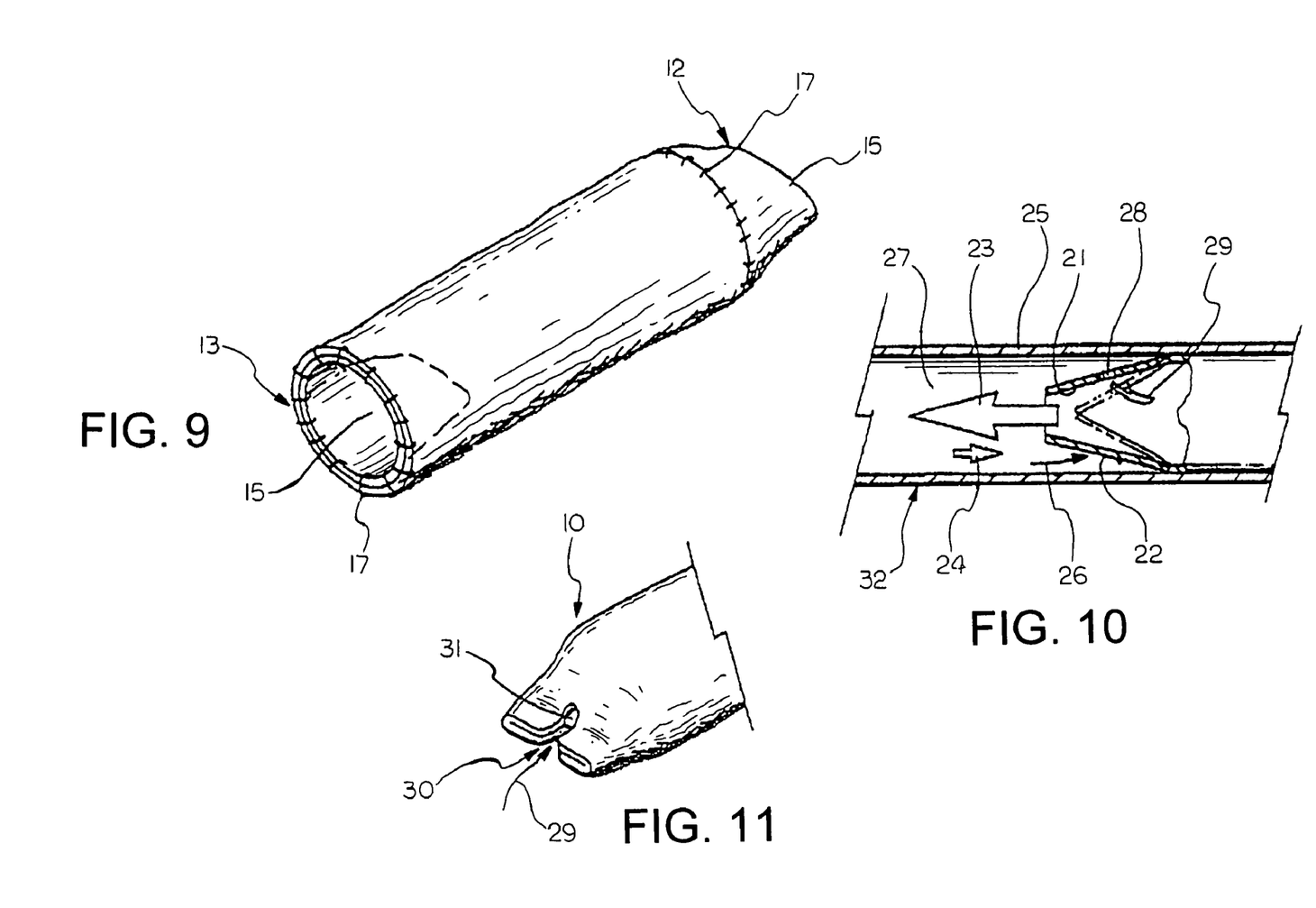
FIG. 9 is a perspective view of a prosthetic valve device according to another embodiment of the invention.
FIG. 10 is a sectional side view of an embodiment with a valve having an opening to permit fluid flow in a second, opposite direction.
FIG. 11 is a partial view of an alternative embodiment with a valve having an opening to permit fluid flow in a second, opposite direction.

Valves are configured to convey, regulate, restrict, or facilitate the flow of bodily fluid by opening and closing temporarily a lumen to permit the movement of fluid through the lumen in a first direction and substantially prevent fluid flow through the lumen and a second, opposite direction. As shown in FIG. 10, valve opening results from muscle contraction, systole, or pressure created by the flow of fluid exerting force on an inner face 21 of the valve, thereby forcing the valve 15 open toward the vessel wall 25. In the closed position, the valve 15 substantially prevents fluid flow in a second, opposite direction 24. Valve closing may result from the muscle relaxation, diastole, or a pressure change, in which case the flow of fluid exerts a force 26 on an opposite face 22 of the valve, thereby forcing the valve 15 away from vessel wall 25 and across the lumen of the vessel 27. In the closed position, the valve 15 may also be configured, as with an opening 28 for example, to permit a relatively small quantity of fluid 29 to flow in a second, opposite direction when the valve is in a closed position without turning inside out.

As shown in FIGS. 10 and 11, embodiments of the device may be adapted to permit fluid flow in a second, opposite direction 29 that is referred to as retrograde flow. In FIG. 10, in the open position, a valve 15 permits fluid flow in a first direction 23, but an opening 28 is adapted to permit retrograde flow 29. FIG. 11 is an alternative embodiment of a prosthetic valve device 10 allowing retrograde flow 29 by forming an opening 30 in the valve 15 to provide a passageway 31 through which a small retrograde flow 29 can pass.

By moving between open and closed positions, the valve 15 allows the regulation of fluid flow through the vessel lumen 27 by providing a valving function. Embodiments of the prosthetic valve device may include a prosthetic venous valve. However, the device 10 could be used for purposes other than vascular purposes.

Multiple Valves

Embodiments may have one or more valves.

FIG. 2 shows a perspective view of an embodiment of a device with more than one valve 15 and 15' formed from the main body 11. FIG. 2 is similar to FIG. 1 except that valves are disposed at both the first and second ends 12, 13.

FIG. 9 shows an embodiment of a device having valves 15 and 15' disposed at the first 12 and second 13 ends of the main body by attachment 17 such as sewing, adhesives, wires, tissue welding, chemical cross-linking, heat source, light source, radiofrequency, lasering, or other energy source. Embodiments may also include a combination having both an attached valve and a valve formed from the main body.

Figure 4A:
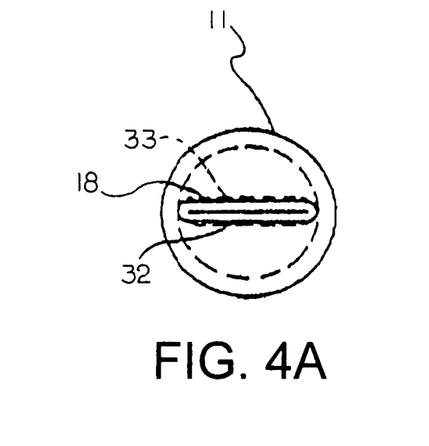
FIG. 4A is an end view of FIG. 2 with valves substantially in line.
Figure 4B:
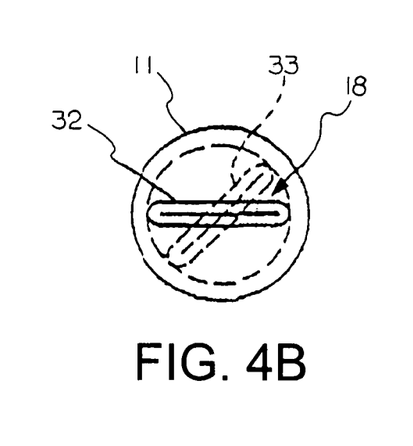
FIG. 4B is an end view of an alternative embodiment of FIG. 2 with offset valves.
Figure 4C:
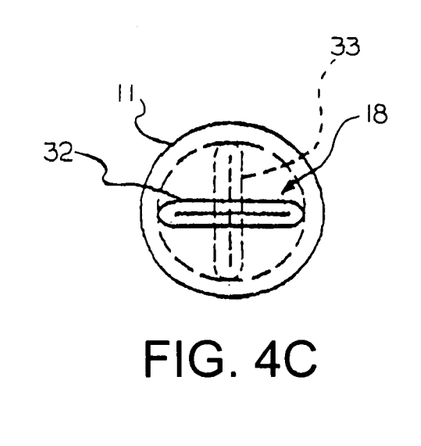
FIG. 4C is an end view of an alternative embodiment of FIG. 2 with offset valves.

As shown in FIGS. 4A, 4B, and 4C, when embodiments have multiple (e.g., two or more) valves, the valves may be substantially in line, offset, or a combination thereof. FIG. 4A is an end view of an embodiment in accordance with FIG. 2. FIG. 4A illustrates in line valves, which are substantially in a common plane or parallel. In other words, in an end-on view of two in line valves, the valve 32 (proximal) is upstream of the fluid flow first direction. The proximal valve 32 eclipses or approximately eclipses the valve 33 that is downstream (distal) to the fluid flow.

FIGS. 4B and 4C illustrate alternative embodiments of FIG. 2 where, in contrast to substantially in line valves, the valves 32, 33 are angularly offset, such as 90° offset from the plane of the other or offset between 0° and 90°. In other words, in an end-on view of two offset valves, the proximal 32 and distal 33 valves would be in a gauche (or staggered) conformation.

For devices with valves that are offset, substantially in line, or a combination, one or more of the multiple valves 15 individually may be adapted with an opening 28, for example, to permit a relatively small quantity of fluid 29 to flow in a second, opposite direction. A prosthetic valve device with multiple valves may include a prosthetic venous valve.

Inverting

Figures 3A, 3B, 3C:
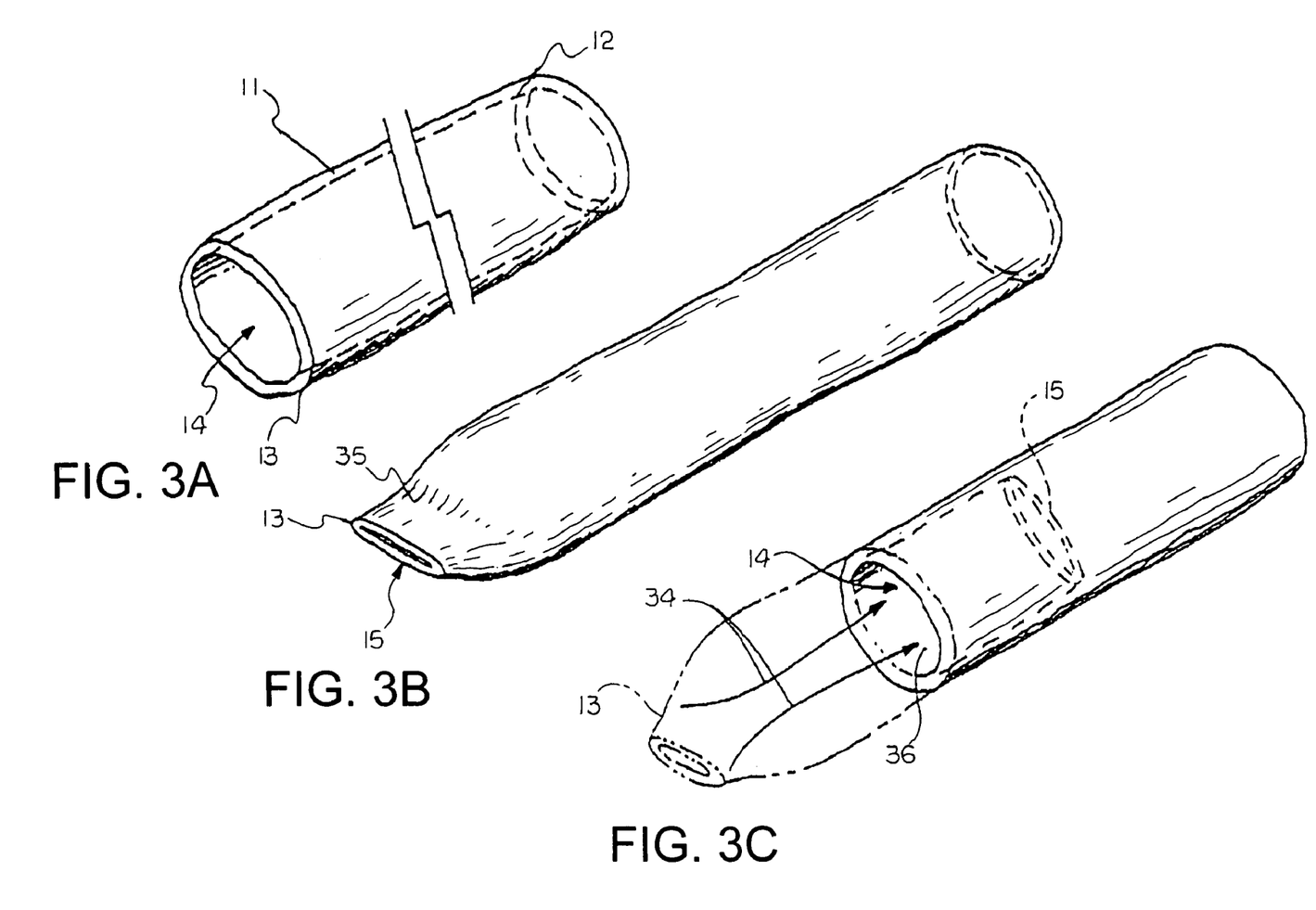
FIG. 3A is a perspective view, broken away, of a main body of a device according to the invention.
FIG. 3B is a perspective view of a main body of a device according to the invention with a valve disposed at one end.
FIG. 3C is a perspective view of the main body illustrated in FIG. 3B with a valve disposed at one end inverted into the lumen of the main body.
Figure 3D:
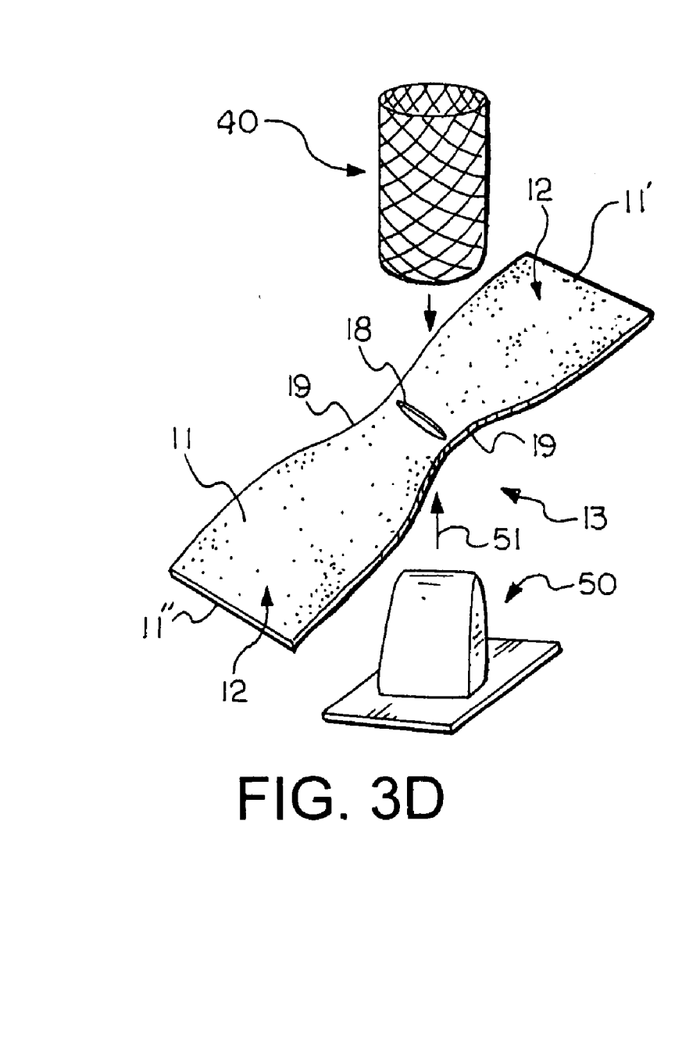
FIG. 3D is a schematic view of a main body sheet inverted to form a prosthetic valve device.
Figure 3E:
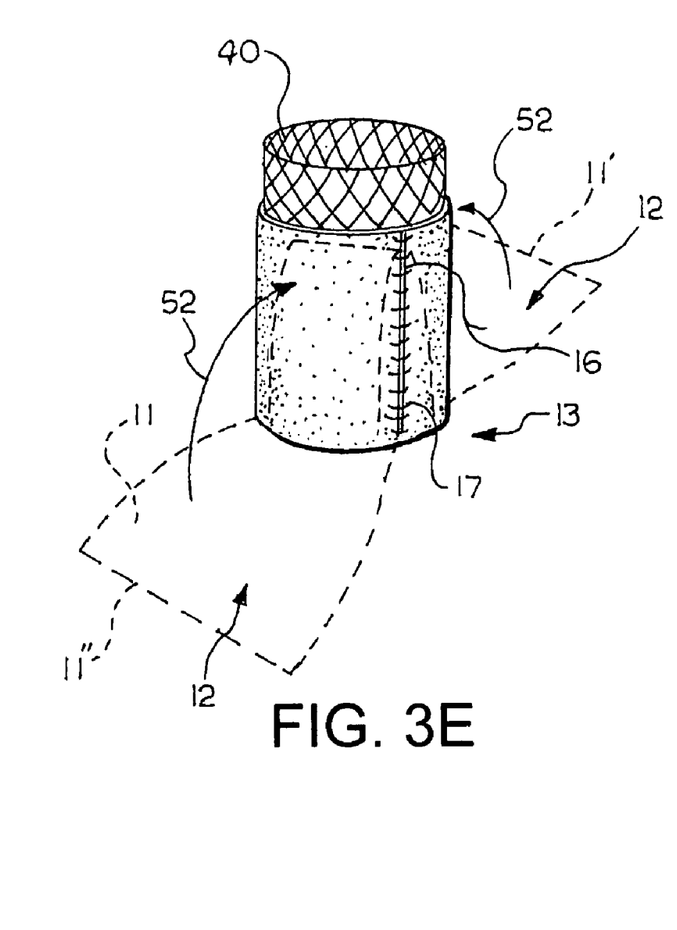
FIG. 3E is a schematic view of the main body of FIG. 3D inverted to form a prosthetic valve device.

FIGS. 3A–3C show embodiments being formed by inversion. FIG. 3A has a main body 11, a first end 12 and a second end 13, and a lumen. FIG. 3B shows an embodiment similar to FIG. 3A except that it includes a valve 15 formed at the second end 13 before inversion. FIG. 3C is an embodiment similar to FIG. 3B except the second end 13 (before or after valve 15 formation) is being inverted in the direction of the arrows 34 into the lumen 14. It should be understood that FIGS. 3A–3C need not be performed sequentially. For instance, the manufacture of a prosthetic valve device may omit the step illustrated in FIG. 3B and, instead, go from FIG. 3A to 3C whereby the valve 15 formation occurs during or after inverting the main body. The valve may be created by the inherent geometry of the inverted tube, or a secondary process after inversion by any suitable means for forming a valve such as molding, altering geometries, by vacuum pressing, or by attachment of a valve.

Inverting 34 describes the structure or step by which material such as one of the first and second ends 12, 13 of the main body is infolded (e.g., tucked, folded inward, turned outside in, rolled inward, folded toward the inside of the tubular structure, inverted into the lumen, inserted into the lumen, or otherwise gathering and securing material in these described directions). In other words, the outer surface 35 of a portion of the second end 13 of the main body 11 will be inside the lumen 14, where a portion of the inverted material forms a second, inner wall 36.

FIGS. 3D and 3E are schematics of embodiments being formed by inversion of a main body sheet material 11 to form a prosthetic valve device. The main body sheet 11 of these embodiments may be made of any suitable material listed above, such as SIS for example, and includes first and second edges 11', 11". The main body is shown as rectangular, but it could be other dimensions including but not limited to circular butterfly or oval or the like, thereby making it clear to include a main body sheet having a continuous circumference whereby opposing sections are defined as first and second edges 11', 11".

The main body 11 of the embodiments of FIGS. 3D and 3E has a middle portion 13 (intermediate portion) that is intermediate the first and second edges 11', 11". The section of the main body called the intermediate portion 13 is for the convenience of the reader viewing the drawings such that the term "intermediate" is intended to mean between, though not necessarily equidistant to, the first and second edges 11', 11". As shown in FIG. 3D, a sheet of main body 11 optionally have a pre-formed slit 18 and optional intents 19.

Inverting (as shown by the arrow 51 in FIG. 3D) the intermediate portion 13 of the main body and folding (as shown by the arrows 52 in FIG. 3E) the first and second edges 11', 11" forms a tubular body as previously defined having a valve (not shown). For example and not by way of limitation, the intermediate portion 13 is positioned on a form 50 for inversion into a frame 40 in FIG. 3D, which frame can be any mold, tubular apparatus, or support structure 40 (as support structure is defined below), and the first and second edges 11', 11" are folded 52 as shown in FIG. 3E and joined (not shown in FIG. 3D but illustrated in FIG. 3E) by any suitable means for joining, such as anchor points 16 or attachment 17 as previously described, including but not limited to sewing, adhesives, wires, bands, tissue welding, chemical cross-linking, heat source, light source, radiofrequency, lasering, or other energy source. Alternatively, the main body may be formed from two or more sheets as previously described, including but not limited to comprising rectangular, circular, butterfly, oval or other configurations of a main body sheet material or combination thereof.

The slit 18 of FIG. 3D, which may be formed by an incision or a cutout of the main body 11 before or after inversion, when assembled may yield a relatively taut or loose valve as desired. FIG. 3E is a schematic view of the main body 11 of FIG. 3D at a further step of assembly. Using inversion as shown in FIGS. 3D and 3E, a taut or loose orifice can be obtained. An alternate embodiment of the main body 11 may be without intents 19 so as to yield a looser valve (not shown), which is just one of many examples of creating a looser valve.

Figure 5:
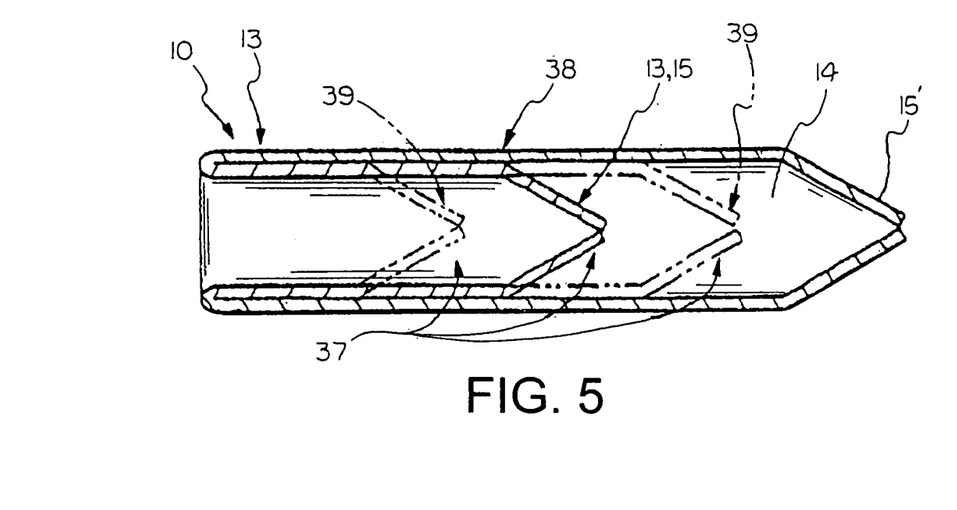
FIG. 5 is a longitudinal sectional view of various axial positions for a valve disposed at the inverted end of the main body.

Referring to the device shown in FIG. 5, the second end 13 may be inverted to various axial lengths 37 within the lumen 14, resulting in valves at different points along the length of the device 10. FIG. 5 shows that a valve may be at the midpoint 38 of the main body or biased on either side 39 of the midpoint. In order to control prolapse, the valves 15 and 15' may be anchored to the main body 11 by anchor points 16 (not shown, but discussed above), may comprise material that may be made (or capable of being made) sufficiently pliable yet strong and rigid enough to control prolapse, may be anchored to the vessel, or may be anchored to the support structure discussed next.

Support Structure

The prosthetic valve device 10 may include a support structure 40 (such as a stent, by way of example only). The specific support frame chosen will depend on numerous factors, including the vessel in which the device is being implanted, the axial length of the treatment site, the number of valves desired, the inner diameter of the vessel, the delivery method for placing the support frame and valve, and others. Those skilled in the art can determine an appropriate support frame based on these various factors. Furthermore, the inner diameter of the support structure need not be constant. For example, the support structure optionally has a sinus (not shown) at or near the site where a valve will be placed, whereby there is a bulging or bowing (e.g., a nominal increase in the inner diameter) of the support structure at or near the site of a valve.

The support structure can be made of any suitable biocompatible material, or should be able to be made biocompatible and/or biocompatible such as by coating, chemical treatment, or the like. Optionally, the support structure material may be bioabsorbable or able to be made bioabsorbable. Examples of suitable materials include, without limitation, stainless steel, nickel titanium (NiTi) alloys, e.g., nitinol, other shape memory and/or superelastic materials, polymers, and composite materials. Stainless steel and nitinol are particularly preferred materials due to their biocompatibility and shapeability. A support structure 40 can be any structure adapted to provide support to the main body. For example, the cross-section of the support structure 40 may be circular, square, rectangular, triangular, crescent, oval, T-shaped, U-shaped, or any configuration to accommodate the main body defining a lumen. Suitable support structures can also have a variety of other configurations, including tubular, braided strands, helically wound strands, ring members, consecutively attached ring members, and frames cut from solid tubes.

Figure 6A:
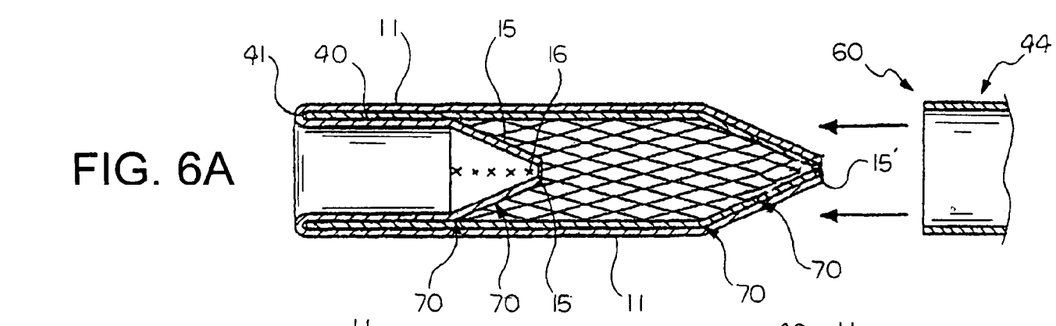
FIG. 6A is a longitudinal sectional view of a support structure and inverted end of the main body, together with an optional additional support frame.
Figures 6B, 6C, 6D:
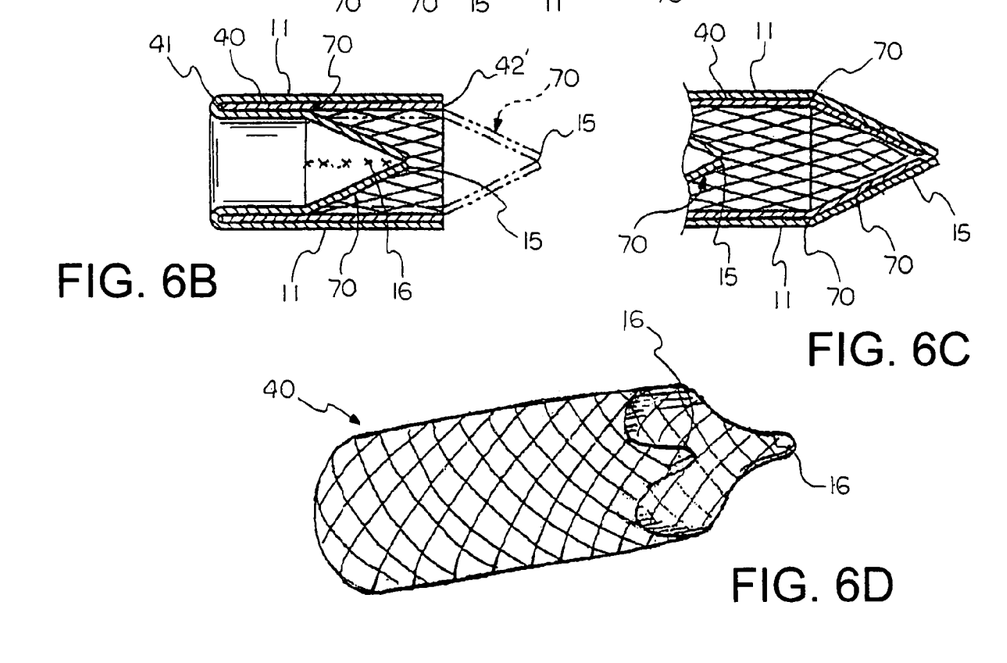
FIG. 6B is an alternative embodiment of a support structure and inverted end of the main body showing a valve positioned intermediate the proximal and distal ends of a support structure or in phantom extending beyond a distal end of the support structure.
FIG. 6C is a perspective view, broken away, of a support structure and inverted main body valve positioned intermediate the proximal and distal ends of a support structure and a valve positioned at the support structure distal end.
FIG. 6D is a three dimensional schematic view of an alternative embodiment of a support structure of FIGS. 6A, 6C, and 8B.

FIG. 6A shows an embodiment comprising a support structure 40 having proximal and distal ends 41, 42. The support structure 40 may be adapted to provide support to the main body 11. FIG. 6B is an alternate embodiment of FIG. 6A showing that a valve disposed at the second end of the main body may be positioned at various locations with respect to the distal end 42 of the support structure 40. For instance, viewing FIG. 6B from left to right, there are two alternative positions of the valve 15 formed at the second end: It may be between proximal and distal ends 41, 42' of the support structure (shown as the left valve) or it may be distal to the distal end 42' of the support structure (shown as the valve in phantom). In addition, the distal end 42' of the support structure 40 may be extended to the right of the current 42' toward the first end. FIG. 6C shows an embodiment having a first valve 15 positioned intermediate the proximal and distal ends 41, 42' of the support structure and a second valve 15' disposed at the first end of the main body. FIG. 6D is three dimensional schematic view of a support structure 40 for the embodiment of FIGS. 6A, 6C, and 8B. The support structure has optional anchor points 16.

The main body may be disposed adjacent to the support structure without being attached. If attached, then attachment of the support structure 40 and the main body 11 may be attached, as illustrated in FIGS. 6A–6C, at attachment points 70 (and/or via anchor points 16 as previously described). Various illustrative locations for attachment points 70 are shown in FIGS. 6A–C, but it should be understood that these are only illustrations. The valve, main body, and/or first or second ends of the main body may be attached to the support structures at other attachment points 70, and each attachment point 70 may represent one or multiple attachment points.

Attachment of the support structure 40 and the main body 11 may be carried out by any suitable means, including but not limited to sewing, adhesives, wires, bands, crimping, tissue welding, chemical cross-linking, heat source, light source, radiofrequency, lasering, or other energy source. As an alternative to attachment, it should be understood that attachment points 70 (and/or via anchor points 16 as previously described) may be omitted at, for example, the valve apex if the valve is sufficiently pliable yet strong and rigid enough to prevent an accordion effect—inverting or everting, sliding, prolapse—of the valve and main body material.

FIG. 6A further shows an optional additional support frame 44. A connection member 60 (including but not limited to sutures, wires, staples, crimping, band(s), and/or adhesives, or if the main body is protected by a sheath or template, then lasering, welding, or other energy source) could be used to connect the optional support frame 44 to the support structure 40, or to the apex of the valve 15 of the first end of the main body, or to the first end of the main body. The optional support frame 44 prevents collapse of the support structure when pressurized and provides leaflet protection.

Figure 7:
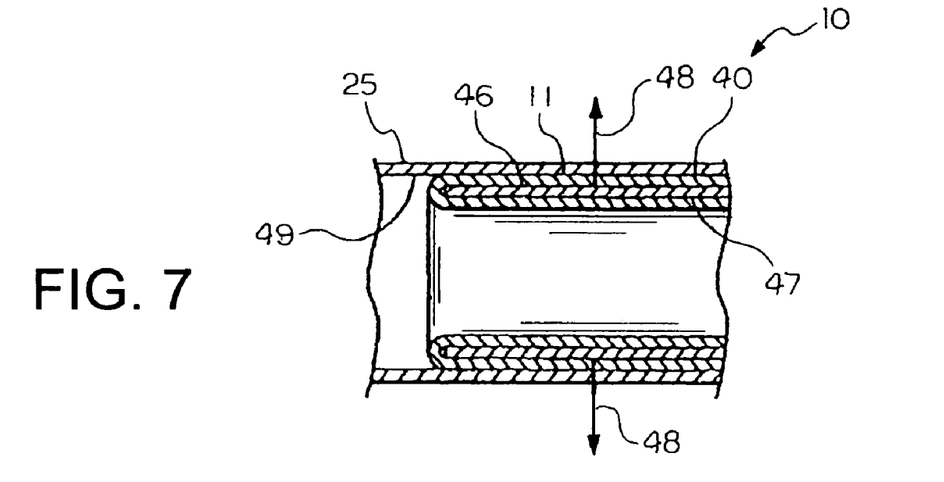
FIG. 7 is a longitudinal sectional view of a prosthetic valve device according to another embodiment of the invention.

FIG. 7 shows a longitudinal (side) view of the proximal end of an embodiment of FIGS. 6A, 6B, or 6C. FIG. 7 shows the relationship between the support structure and the main body, which is now explained.

As shown in FIG. 7, the proximal end of the support structure 40 may be enveloped by a portion of the main body 11 in that the main body 11 is disposed internal and external 47, 46 to the support structure 40. Therefore, the support structure 40 exerts a radially outward force 48 on the main body 11 and on the interior surface 49 of the vessel wall 25.

Figure 8A:
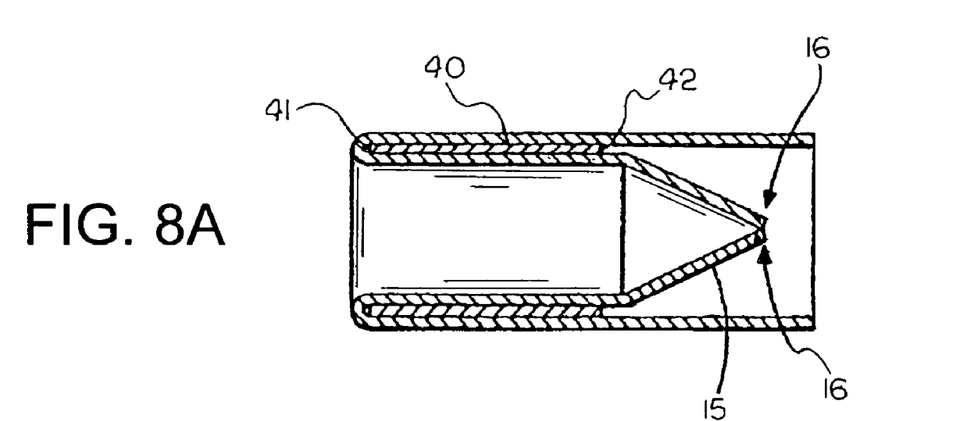
FIG. 8A is a longitudinal sectional view of an embodiment with a valve positioned so as to extend beyond a distal end of a support structure.
Figure 8B:
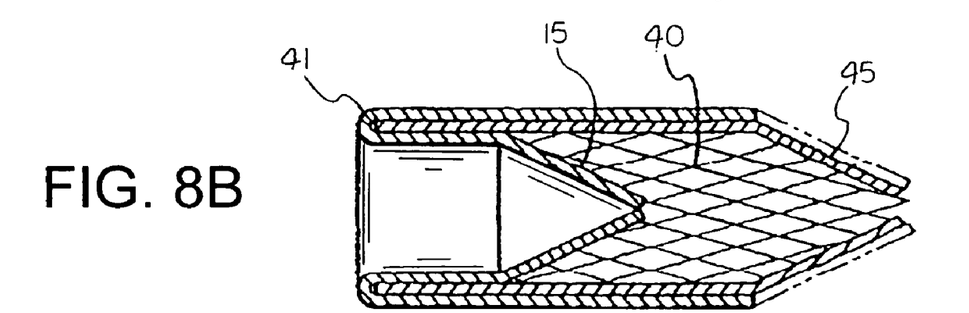
FIG. 8B is a longitudinal sectional view of an embodiment with a valve positioned between proximal and distal ends of a support structure together with an optional second valve positioned at the support structure distal end.

FIGS. 8A and 8B should be understood as showing, where an embodiment has a support structure and only one valve, that one valve 15 may be positioned intermediate the proximal 41 and distal 42 ends of the support structure as in FIG. 8B, or extending beyond the distal end 42 of the support structure as in FIG. 8A. FIG. 8A further shows that a valve 15 may be distally extended beyond a distal end 42 of a support structure 40 (and optional anchor points 16 near the valve orifice are utilized to control prolapse), whereas a valve 15 shown in an embodiment depicted in FIG. 8B is positioned between the proximal and distal ends 41, 42 of a support structure 40. As shown in FIG. 8B, a second valve 45 (in phantom) may be formed at the first end of the main body 11, where the first and second valves 15, 45 are either angularly offset or substantially in line. (Attachment points 70 are not shown but are present in FIGS. 7, 8A, and 8B).

Methods

The invention also comprises methods of making prosthetic valve devices for implantation in a body vessel.

Figure 12:
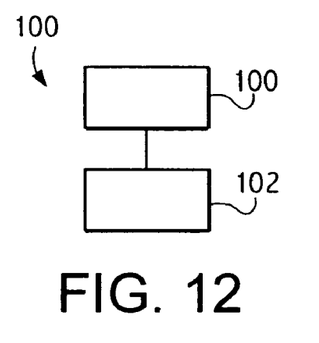
FIG. 12 is a block diagram illustrating a method of the invention.

FIG. 12 is a block diagram of a method of manufacturing a prosthetic valve device. A tubular main body 11 is provided (step 101) having first and second ends and defining a lumen. The second end is inverted (step 102) into the lumen to form a valve before, during, or after inversion. In the alternative, a sheet of main body 11 is provided (step 101), as described above relating to FIGS. 3D and 3E and which discussion is incorporated by reference, having first and second ends. The sheet of main body 11 optionally may have a pre-formed slit 18 and optional intents 19 as described above. The main body intermediate the first and second ends is inverted (step 102) to form a tubular body having a lumen and a valve. For example only and not by way of limitation, step 102 may be performed by placing the main body over a form 50 for inversion and joining the edges of the main by any suitable means such as anchor points 16 or attachment 17 as previously described.

Figure 13:
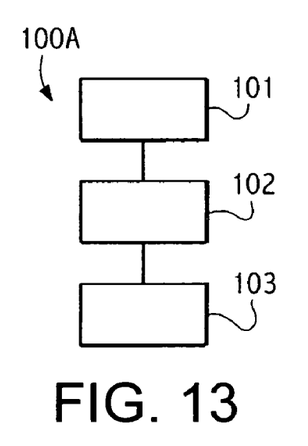
FIG. 13 is a block diagram illustrating another method of the invention.

As shown in FIG. 13, an alternative method 100A of making a prosthetic valve device is provided. In one embodiment, a main body having first and second ends and defining a lumen is provided (step 101). A valve at the second end of the main body is formed (step 102). The second end of the main body is inverted into the lumen (step 103). In an alternative method, a valve may be formed at the first end (step 102); as a further alternative method, forming a valve includes attaching a valve to the main body (step 102).

Figure 14:
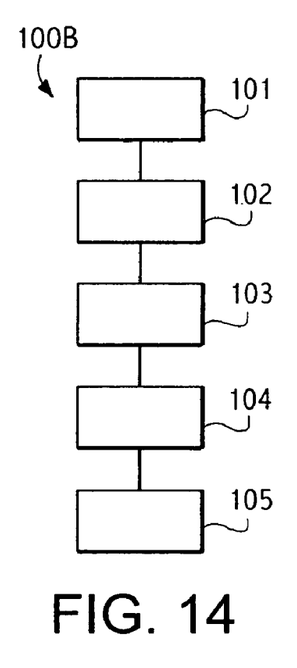
FIG. 14 is a block diagram illustrating another method of the invention.

As shown in FIG. 14, an alternative method 100B of making a prosthetic valve device may include providing a support structure. This method is similar to the method of FIG. 13. In addition, a method in accordance with FIG. 14 includes providing a support structure having proximal and distal ends (step 104). FIG. 14 further includes disposing the proximal end of the support structure in the lumen of the main body (step 105). Inverting the second end of the main body to the lumen envelopes the proximal end of the support structure (step 103).

A method of making a prosthetic valve device may include forming multiple valves from the main body (step 102). For example, a valve may be formed at the first and second ends of the main body (step 102). Alternatively, it should be understood that forming as used in the method may include attaching one or more valves (step 102).

A method of making a prosthetic valve device does not need to be performed sequentially. In FIGS. 13 and 14, for example, a first or second end of the main body may be inverted (step 103) before a valve is formed (step 102) internal to the main body, or the valve may be formed (step 102) before inversion (step 103). Also, when a support structure is provided (step 104), the valve could be formed (step 102) before or after disposing (step 105) the support structure in the lumen of the main body. Alternatively in a method that includes a support structure, the second end of the main body could be inverted (step 103) before or after the support structure is disposed (step 105) in the lumen of the main body and its proximal end is enveloped by the second end of the main body.

FIGS. 3A through 3C, by way of example only, show an embodiment of a prosthetic valve device made in accordance with one method. FIG. 3A illustrates providing a main body 11 having first and second ends 12, 13 and defining a lumen 14 (step 101). FIG. 3B shows a valve 15 is formed at the second end 13 (step 102). FIG. 3C is an embodiment similar to FIG. 3B except the second end 13 (before or after valve 15 formation (step 102)) is being inverted in the direction of the arrows 34 into the lumen 14 (step 103). Although FIGS. 3A–C are discussed, this description is by example only and is not to be limiting. Other embodiments of prosthetic valve devices may be made by the methods taught herein, such as providing a support structure, disposing the support structure in the lumen of the main body, and/or forming multiple valves, which are shown in the other figures contained herein.

FIGS. 3D and 3E, also by way of example only, show an embodiment of a prosthetic valve device made in accordance with one method. A method of forming a prosthetic valve device includes providing (step 101) a sheet of main body 11 material having first and second ends. The sheet of main body 11 optionally may have a pre-formed slit 18 and optional intents 19 as described above. The main body intermediate the first and second ends is placed about a form 50 (step 102) to shape into a tubular body having a lumen and a valve. The edges of the main body are joined (step 103) by any suitable means such as anchor points 16 or attachment 17 as previously described.

It is intended that the foregoing detailed description of the prosthetic valve devices and methods of making such devices be regarded as illustrative rather than limiting, and that it be understood that it is the following claims, including all equivalents, that are intended to define the spirit and scope of this invention. Therefore, the embodiment of any figure and features thereof may be combined with the embodiments depicted in other figures. Other features known in the art and not inconsistent with the structure and function of the present invention may be added to the embodiments.

We claim:

1. A prosthetic valve device for implantation in a body vessel, comprising:
   a tubular main body having first and second ends and defining a lumen;
   a prosthetic valve disposed at the second end, the valve adapted to permit fluid flow through the lumen in a first direction and substantially prevent fluid flow through the lumen in a second, opposite direction;
   a support structure having proximal and distal ends, the proximal end disposed in the lumen of the main body, the second end of the main body and prosthetic valve disposed at that second end are inverted into the lumen such that the main body second end envelops the proximal end of the support; and
   wherein the valve extends distal the support structure distal end.

2. The device of claim 1 wherein said prosthetic valve device comprises a prosthetic venous valve.

3. The device of claim 1 wherein the valve comprises a biscuspid valve.

4. The device of claim 3 wherein the valve is formed without longitudinal incisions.

5. The device of claim 1 wherein the valve is axially positioned between the support structure proximal end and the support structure distal end.

6. The device of claim 1 wherein the valve is located at or near the support structure distal end.

7. The device of claim 1 further comprising one or more attachment points that attach the support structure and the main body.

8. The device of claim 7 wherein the attachment points attach the support structure proximal end and the main body second end at or near the valve.

9. The device of claim 1 wherein the prosthetic valve disposed at the main body second end is formed from the main body.

10. The device of claim 1 wherein the prosthetic valve disposed at the main body second end is attached to the main body second end.

* * * * *

UNITED STATES PATENT AND TRADEMARK OFFICE
CERTIFICATE OF CORRECTION

PATENT NO. : 7,153,324 B2
APPLICATION NO. : 10/909153
DATED : December 26, 2006
INVENTOR(S) : Brian C. Case, et al.

It is certified that error appears in the above-identified patent and that said Letters Patent is hereby corrected as shown below:

Col. 13, line 2-17; should read
1. A prosthetic valve device for implantation in a body vessel, comprising: a tubular main body having first and second ends and defining a lumen; a prosthetic valve disposed at the second end, the valve adapted to permit fluid flow through the lumen in a first direction and substantially prevent fluid flow through the lumen in a second, opposite direction; a support structure having proximal and distal ends, the proximal end disposed in the lumen of the main body, the second end of the main body and prosthetic valve disposed at that second end are inverted into the lumen such that the main body second end envelops the proximal end of the support <u>structure</u>; and wherein the valve extends distal the support structure distal end.

Signed and Sealed this

Third Day of July, 2007

JON W. DUDAS
*Director of the United States Patent and Trademark Office*